United States Patent [19]

Kötzsch et al.

[11] 4,161,486
[45] Jul. 17, 1979

[54] CLEAVAGE OF SILICON-TO-CARBON BONDS BY MEANS OF HYDROGEN HALIDE

[75] Inventors: Hans-Joachim Kötzsch; Rüdiger Draese; Hans-Joachim Vahlensieck, all of Rheinfelden, Fed. Rep. of Germany

[73] Assignee: Dynamit Nobel Aktiengesellschaft, Troisdorf, Fed. Rep. of Germany

[21] Appl. No.: 880,903

[22] Filed: Feb. 24, 1978

[30] Foreign Application Priority Data

Feb. 26, 1977 [DE] Fed. Rep. of Germany ....... 2708406

[51] Int. Cl.² .................................................. C07F 7/12
[52] U.S. Cl. ............................................. 260/448.2 E
[58] Field of Search ................................. 260/448.2 E

[56] References Cited

U.S. PATENT DOCUMENTS 4,053,495 10/1977 Deinhammer ................ 260/448.2 E

*Primary Examiner*—Paul F. Shaver
*Attorney, Agent, or Firm*—Sprung, Felfe, Horn, Lynch & Kramer

[57] ABSTRACT

In a process for preparing a halogen alkyl silane by contacting an alkyl silane of the formula $$R_nSiR'_{4-n}$$

wherein
R represents a substituted or unsubstituted alkyl or alkenyl group,
R' represents an alkyl group, and
n represents 0, 1, or 2 with a hydrogen halide in the presence of a catalyst, the improvement which comprises employing as the catalyst an aluminum oxide-containing composition.

6 Claims, No Drawings

4,161,486

CLEAVAGE OF SILICON-TO-CARBON BONDS BY MEANS OF HYDROGEN HALIDE

BACKGROUND OF THE INVENTION

1. Field of the Invention

The present invention relates to the cleavage of the silicon-to-carbon bond by means of hydrogen halide, with the formation of a silicon-to-halogen bond. The carbon atom bound to the silicon in this case is a component of an alkyl group, so that by means of this method it is possible to prepare halogen alkyl silanes from alkyl silanes.

2. Discussion of the Prior Art

It is known in the case of tetraalkyl silanes to cleave a silicon-to-carbon bond by means of hydrogen halide by using Friedel-Crafts catalysts, especially anhydrous aluminum chloride. The use of this catalyst, however, has several disadvantages. Aluminum chloride is soluble in the chloralkyl silanes, so that the reaction has to be followed by a separation of the catalyst from the reaction product. Separation by distillation runs into difficulties because the catalyst remains as a sludge in the sump of the distillation apparatus and, as the distillation progresses, it constantly leads to clogging due to sublimation. Consequently, in this method of procedure, yields of pure product are obtained which amount to only about 62 percent.

The filtration of the aluminum chloride also runs into difficulties. Consequently, it has also been previously proposed to precipitate it as a complex compound with phosphorus hydroxychloride and then filter it out. This procedure is difficult and requires two additional steps.

It is an object of this invention, therefore, to provide a process for the replacement of an alkyl group of an alkyl silane by a halogen, which process can be readily performed to directly provide the desired product in a high yield, especially a yield of more than 90 percent of haloalkyl silane. More especially, it is an object of this invention to provide a process for the preparation of haloalkyl silanes, especially chloralkyl silanes where the product can be obtained without extensive recovery procedures to separate out the desired product from the reaction medium.

SUMMARY OF THE INVENTION

In accordance with the present invention, there is provided an improved process for the preparation of a halogen alkyl silane by contacting an alkyl silane of the formula

where
- R represents an unsubstituted or substituted alkyl moiety, especially one of 1 to 8 carbon atoms, or an alkenyl moiety of 2 to 8 carbon atoms,
- R' represents an alkyl moiety, especially one of 1 to 10 carbon atoms, preferably 1 to 5 carbon atoms, and
- n can be 0, 1, or 2, with a hydrogen halide in the presence of a catalyst, the invention residing in employing as the catalyst aluminum oxide or an aluminum oxide-containing composition.

In accordance with this invention, it has been found that exceptionally high yields of halogen alkyl silanes can be obtained by replacement of an alkyl group of an alkyl silane with a halogen atom from a halogen halide if the catalyst employed for the reaction is aluminum oxide or an aluminum oxide-containing composition. In particular, high yields of chloralkyl silanes are obtained in accordance with the claimed process.

By means of the catalyst of the invention, one can perform the reaction with virtually quantitative yields. Virtually no secondary reactions occur. The catalyst is insoluble in the reaction products, so that the separation of the desired chloralkyl silane can be accomplished easily by known methods.

The catalyst is aluminum oxide, which can be either the synthetic or the naturally occurring product. Accordingly, clay, corundum, or oxidic aluminum ores such as mica, can be used as catalysts in accordance with the invention. It is necessary, of course, that the aluminum oxide mineral does not react with hydrogen halide.

Other aluminum oxide-containing compositions which are also useful include both natural and synthetic crystalline aluminosilicates, especially aluminosilicate zeolites.

The alkyl silanes usable as starting substances include both unsubstituted and substituted alkyl silanes. It is important that at least one alkyl group be unsubstituted. The substituents are mainly halogens. However, amino or carbonyl groups, for example, can also be substituents. Also, one or two of the alkyl groups can be replaced by an alkenyl group, such as the vinyl or the allyl group, for example. Examples of compounds which come under the definition given are tetramethylsilane, chloromethyltrimethylsilane, tetraethylsilane, vinyltrimethylsilane, tetrapropylsilane, 3-chloropropyltrimethylsilane and tetrabutylsilane. These examples of compounds demonstrate that the substituent preferable is on the end of the chain.

The preferred hydrogen halide is hydrogen chloride. It is used in stoichiometric amounts, i.e., one mole of hydrogen chloride per mole of alkyl silane. It is recommended, however, to use the alkyl silane in a slight excess (up to a maximum of about 10 percent).

It is desirable to perform the reaction by preparing a uniform mixture of the starting substances and passing this mixture continuously through the catalyst. The catalyst is in a solid bed or in a fluidized bed. The reaction is exothermic. It is mostly only the monochloroalkyl alkyl silane that forms. The formation of di- or trichloralkyl alkyl silanes has not been observed, even when an excess of hydrogen halide was used.

The time of stay on the catalyst can amount to between one second and 70 minutes. It is preferably between 12 seconds and 25 minutes. The mixture passed through the catalyst can be either in the liquid or in the gaseous aggregate state. Preferably, however, it is gaseous. In this case it is sometimes necessary to heat the alkyl silane before the mixing and to pass the mixture through the catalyst at temperatures above the boiling point of the alkyl silane.

The reaction temperatures can be between $-50°$ C. and $240°$ C., preferably between $0°$ C. and $120°$ C. Preferably, temperatures are selected which are below the boiling temperature of the desired chloralkyl silane if a solid bed catalyst is used. In the case of a fluidized bed, it is recommended to maintain a reaction temperature above the boiling point of the desired chloralkyl silane.

Both the detention time and the reaction temperature are selected in accordance with the structure of the starting substance. For example, tetramethylsilane reacts in a relatively brief detention time and/or at low temperatures with a strong heat tone to form trimethylchlorosilane and methane in a quantitative yield, whereas on the other hand tetrabutylsilane, for example, at a low reaction heat, requires longer detention times and/or higher temperatures for the quantitative transformation. It is desirable, however, to select the reaction conditions such that a complete transformation of the hydrogen chloride will take place, because this simplifies the working up of the product.

The working up of the reaction products is performed by known methods. In general, distillative refinement is possible and entirely sufficient to obtain pure products.

The solid bed or fluidized bed reactor is advantageously constructed as a cylindrical tube which is provided with a thermostat-controlled jacket.

By the method of the invention it is possible to produce, for example, trimethylchlorosilane, chloromethyldimethylchlorosilane, triethylchlorosilane, vinyldimethylchlorosilane, tripropylchlorosilane, 3-chloropropyldimethylchlorosilane, and tributylchlorosilane. These products are of considerable importance as protective-group reagents. In particular, trimethylchlorosilane finds wide technical application in the production of semisynthetic penicillins and cephalosporins, for the modification of inorganic and organic substances and high polymers, and in the production of silazanes. Especially trimethylchlorosilane has hitherto been unavailable in sufficient quantity, because there has not been any economical method of synthesizing it, and it has been obtained only in small amounts as a by-product in the Rochow synthesis of methyl-substituted chlorosilanes on a large scale.

Furthermore, chloralkyl chlorosilanes, such as, for example, chloromethyldimethylchlorosilane, are used as adhesives in connection with high polymers and fillers.

In order to more fully illustrate the nature of the invention and the manner of practicing the same, the following examples are presented:

EXAMPLES

Example 1

The reactor is a jacketed tube of glass having an inside diameter of 40 mm; cooling water flows through the jacket, and the cylinder is filled with approximately 1.3 liters of 3 mm aluminum oxide pellets (packing length 1000 mm) as the catalyst bed. The catalyst temperature is measured by means of a resistance thermometer and recorded. The solid bed reactor is operated downwardly by feeding the mixture of the two reaction components to the top of the reactor and removing the reaction mixture at the foot of the reactor. The hydrogen chloride gas is fed in through a flow meter and the silane is also fed in gas form through a flow meter that is heated as required. The two reaction components are delivered into a common line after leaving the metering apparatus and fed through a one-liter flask filled with 4 mm glass rings and thermostatically controlled if necessary, which serves as a mixing vessel, before they enter the reactor in the form of a homogeneous mixture.

The reaction mixture emerging from the bottom of the reactor flows into a receiver equipped with a reflux condenser. The receiver collects the liquid reaction product flowing from the reflux condenser and the reactor, while the alkane contained in the reaction product is fed from the top end of the reflux condenser to a gasometer.

The experiment is begun by starting the hydrogen chloride feed at a rate of 2.5 moles of HCl per hour. Two to three minutes later, the silane feed is started with 2.6 moles of vaporized tetramethylsilane per hour, the silane proportioning system and the mixing vessel being temperature controlled at 30° C. The feeding of the reactor thus corresponds to a detention time of 38 seconds (with respect to the empty tube).

The exothermic reaction starts immediately, a catalyst temperature of about 50° to 75° C. establishing itself. The liquid reaction product separates in the liquid receiver, under the reflux condenser operating at −42° C., while the methane formed in the reaction collects in the gasometer.

During a continuous operating period of 272 hours, 72.52 kg of trimethylchlorosilane (B.P. 57° C.) and 16.4 $Nm^3$ of methane (approx. 10.9 kg) are obtained. The transformation of the hydrogen chloride charged is quantitative. 2.36 kg of tetramethylsilane (B.P. 26° C.) is isolated and recovered, and is fed back into the process. The total consumption of starting substances is 59.84 kg of tetramethylsilane and 24.8 kg of hydrogen chloride, so that the yield of trimethylchlorosilane is 98.2% with respect to tetramethylsilane and 98.4% with respect to the hydrogen chloride. Approximately 0.2% of tetrachlorosilane constitutes the only secondary product.

EXAMPLE 2

As in Example 1, a reactor having an inside diameter of 25 mm, filled with approximately 0.25 liter of 3 mm pellets of aluminum oxide (catalyst bed length 1000 mm), is fed a mixture of 2.5 moles of hydrogen chloride and 2.6 moles of tetramethylsilane per hour, corresponding to a detention time of about 14 seconds, the catalyst temperature varying from about 68° to 87° C., and 24.4 kg of trimethylchlorosilane and 5.4 $Nm^3$ of methane (approx. 3.6 kg) are obtained after continuous operation for 90 hours. The hydrogen chloride transformation is again quantitative. Approximately 800 g of tetramethylsilane is recovered by distillation and reused. Again, about 0.2% of tetrachlorosilane is the only secondary product.

EXAMPLE 3

As in Example 1, 1 mole of hydrogen chloride and 1.03 moles of chloromethyltrimethylsilane (B.P. 98° C.) are charged per hour. The silane proportioning means and the mixing vessel are temperature-controlled at 103° C. and the reactor at 100° C. The detention time is about 2 minutes. A catalyst temperature between 133° C. and 147° C. establishes itself.

Over a continuous period of 12 hours of operation, 1682 g of chloromethyldimethylchlorosilane (B.P. 114° C.) and about 270 Nl of methane (approximately 190 g) are obtained. The transformation of hydrogen chloride is quantitative. About 37 g of chloromethyltrimethylsilane is recovered by distillation and reused. About 0.6% of tetrachlorosilane is formed as the secondary product. A total of 1477 g of chloromethyltrimethylsilane and 438 g of hydrogen chloride are consumed, so that the yield of chloromethyldimethylchlorosilane is 97.7% with respect to the chloromethyltrimethylsilane and 98% with respect to the hydrogen chloride.

EXAMPLE 4

As in Example 1, 0.1 mole per hour of hydrogen chloride and 0.11 mole per hour of 3-chloropropyltrimethylsilane (B.P. 151° C.) are charged. The silane proportioning means and the mixing vessel are temperature-controlled at 157° C., and the reactor at 150° C. The detention time is about 19 minutes. A catalyst temperature between 154° C. and 161° C. establishes itself.

Over a continuous period of 20 hours of operation, 334 g of 3-chloropropyldimethylchlorosilane (B.P. 179° C.) and about 44.7 Nl of methane (approx. 31 g) are obtained. The hydrogen chloride transformation is quantitative.

About 28 g of 3-chloropropyltrimethylsilane is recovered by distillation and reused. Approximately 0.5% of tetrachlorosilane is formed as by-product. In all, 303 g of 3-chloropropyltrimethylsilane and 73 g of hydrogen chloride are consumed, so that the yield of 3-chloropropyldimethylchlorosilane is 97.5% with respect to 3-chloropropyltrimethylsilane, and 97.7% with respect to hydrogen chloride.

EXAMPLE 5

As in Example 1, 0.2 mole of hydrogen chloride and 0.22 mole of tetra-n-butylsilane (B.P. 231° C.) are charged per hour. The silane proportioning means and the mixing vessel are temperature controlled at 240° C., and the reactor at 70° C. The detention time is about 10 minutes. A catalyst temperature between 103° C. and 108° C. establishes itself. The reflux condenser operates at about 12° C.

During a continuous period of 10 hours of operation, 456 g of tri-n-butylchlorosilane (B.P.$_{12}$ 125°–126° C.) and about 21.7 Nl of n-butane (approx. 56 g) are obtained. The hydrogen chloride transformation is quantitative.

Approximately 55 g of tetra-n-butylsilane is recovered by distillation and reused. About 0.2% of tetrachlorosilane is formed as by-product.

In all, 508 g of tetra-n-butylsilane and 73 g of hydrogen chloride are consumed, so that the yield of tri-n-butylchlorosilane is 98% with respect to tetra-n-butylsilane and 95% with respect to hydrogen chloride.

EXAMPLE 6

In the experimental arrangement described in Example 1, the solid bed reactor is replaced by a fluidized bed reactor consisting of a jacketed glass tube of 50 mm diameter 800 mm high having a centrally disposed 3 mm valve at the bottom as the blowing inlet. The reactor is filled with corundum of a particle size of 0.1 to 0.2 mm to a height of 360 mm when at rest, and it is thermostatically controlled at 70° C. in the jacket. The silane proportioning means and the mixing vessel operate at the same temperature.

As in Example 1, a mixture consisting of 4 moles of hydrogen chloride and 4.1 moles of tetramethylsilane is fed through the blowing valve into the reactor per hour. This input at the rate of about 200 Nl/h corresponds to a blowing velocity of about 2.9 cm/sec (with respect to the empty reactor tube). The fluidized bed is thus expanded to a height of about 410 mm and assumes a reaction temperature of about 82° C. The detention time amounts to about 14 seconds. During a continuous period of 100 hours of operation, 42.8 kg of trimethylchlorosilane and 9.0 Nm$^3$ of methane (approx. 6.4 kg) are obtained. The transformation of the input hydrogen chloride is quantitative.

By distillation, 0.91 kg of tetramethylsilane is recovered for reuse.

The total consumption of starting substances amounts to 34.9 kg of tetramethylsilane and 14.6 kg of hydrogen chloride, so that the yield of trimethylchlorosilane is 98.8% with respect to tetramethylsilane and 98.4% with respect to hydrogen chloride. The only by-product is about 0.1% of tetrachlorosilane.

What is claimed is:

1. In a process for preparing a halogen alkyl silane by contacting an alkyl silane of the formula

$$R_nSiR'_{4-n}$$

where
R represents a substituted or unsubstitued alkyl group or an alkenyl group,
R' represents an alkyl group, and
n represents 0, 1, or 2
with a hydrogen halide in the presence of a catalyst, the improvement which comprises employing as the catalyst aluminum oxide or an aluminum oxide-containing composition.

2. A process according to claim 1 wherein the reactants are continuously drawn into contact with the catalyst for a detention time of from one second to 70 minutes.

3. A process according to claim 1 wherein the reaction is performed in the gaseous phase at a temperature up to 240° C.

4. A process according to claim 1 wherein the catalyst is disposed in a solid bed.

5. A process according to claim 1 wherein the catalyst is employed as a fluidized bed.

6. A process according to claim 1 wherein R represents an alkenyl group substituted by a member selected from Cl-, Br-, J-, H$_2$N- and ROOC-.

* * * * *